US008269983B2

(12) United States Patent
Wadman

(10) Patent No.: US 8,269,983 B2
(45) Date of Patent: Sep. 18, 2012

(54) APPARATUS FOR OBSERVING THE SURFACE OF A SAMPLE

(75) Inventor: Sipke Wadman, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 268 days.

(21) Appl. No.: 12/679,357

(22) PCT Filed: Sep. 23, 2008

(86) PCT No.: PCT/IB2008/053864
§ 371 (c)(1),
(2), (4) Date: Mar. 22, 2010

(87) PCT Pub. No.: WO2009/040732
PCT Pub. Date: Apr. 2, 2009

(65) Prior Publication Data
US 2010/0208273 A1      Aug. 19, 2010

(30) Foreign Application Priority Data

Sep. 24, 2007 (EP) .................................... 07117020

(51) Int. Cl.
G01B 11/30 (2006.01)
G01N 21/55 (2006.01)
A61N 5/01 (2006.01)
(52) U.S. Cl. ................ 356/601; 356/445; 606/9; 606/13
(58) Field of Classification Search .......... 356/445–448, 356/326, 600–601; 250/269.2, 216, 571; 606/9, 13
See application file for complete search history.

(56) References Cited

U.S. PATENT DOCUMENTS

| 4,521,118 | A | * | 6/1985 | Rosencwaig ..................... 374/5 |
| 5,093,580 | A | * | 3/1992 | Sting ...................... 250/559.16 |
| 5,893,364 | A |   | 4/1999 | Haar et al. |
| 5,912,741 | A | * | 6/1999 | Carter et al. ................... 356/445 |
| 6,024,449 | A |   | 2/2000 | Smith |
| 6,032,071 | A |   | 2/2000 | Binder |
| 6,088,087 | A |   | 7/2000 | Graves et al. |
| 6,251,070 | B1 |   | 6/2001 | Khazaka |
| 6,292,532 | B1 | * | 9/2001 | Kawahara et al. ............... 378/49 |
| 6,574,305 | B2 | * | 6/2003 | De Boer et al. ................. 378/83 |
| 7,220,254 | B2 | * | 5/2007 | Altshuler et al. ................ 606/9 |
| 7,872,754 | B2 | * | 1/2011 | Wadman ...................... 356/445 |
| 2002/0016533 | A1 |   | 2/2002 | Marchitto et al. |
| 2002/0091322 | A1 |   | 7/2002 | Chaiken et al. |
| 2004/0169864 | A1 |   | 9/2004 | Carl |
| 2006/0056661 | A1 |   | 3/2006 | Einighammer et al. |
| 2006/0092315 | A1 |   | 5/2006 | Payonk et al. |
| 2006/0239547 | A1 |   | 10/2006 | Robinson et al. |

FOREIGN PATENT DOCUMENTS

| FR | 2821152 A1 | 8/2002 |
| WO | 2006091781 A1 | 8/2006 |
| WO | 2007072403 A1 | 6/2007 |
| WO | 2009040716 A2 | 4/2009 |

* cited by examiner

*Primary Examiner* — Sang Nguyen

(57) ABSTRACT

An apparatus for observing the appearance of a surface of a sample of semitransparent material, the apparatus comprising a light source for illuminating at least a region of interest of the surface of the sample from a predetermined direction and means for observing a response to the illumination of the region of interest, wherein the illuminated region comprises the region of interest and a region surrounding the region of interest. In this way the influence of emitted scattered light on the accuracy of the observation of the appearance of the sample is minimized.

5 Claims, 3 Drawing Sheets

APPARATUS FOR OBSERVING THE SURFACE OF A SAMPLE

FIELD OF THE INVENTION

The invention is related to an apparatus for observing the appearance of the surface of a sample of a semitransparent material.

BACKGROUND OF THE INVENTION

In order to observe the appearance of the surface of a sample, the surface can be viewed from a certain direction, whereby a light beam is directed to the surface from another direction. Thereby, a variety of information about the surface can be obtained, depending on the direction, intensity and color of the incoming and outgoing light and on the direction of viewing towards the surface. The observed appearance may include the texture and/or relief or protrusions or projections of the surface such as hair on the skin and, in case the surface itself is more or less translucent, the texture and/or color and/or morphology underneath the surface, i.e. the subsurface. The observation can be recorded and/or analyzed.

It should be noted that the expression appearance is used in this description for each combination of aspects and/or properties of the surface of the sample and the perception of the observer of it, including the relief of the surface, the color of the surface, the light reflecting and light absorbing properties of the surface, etc. Observing is a general expression, it may include inspecting and/or recording and/or analyzing of the appearance of the surface.

A non-contact and non-perturbing monitoring technique is useful in many areas of technology to determine surface and/or sub-surface morphology. Furthermore, the type and density of material defects or other features, which have a geometric shape, can be characterized using this technique. Another use of this technique is the analysis of the characteristics and condition of human skin.

In particular when details of the morphology are to be analyzed, it is desired to make observations of the appearance of the surface from different directions, whereby the light source also may illuminate the surface from one or more predetermined directions (different angles with respect to the plane of the surface).

In particular when the surface of a relative large object has to be observed, for example a piece of the skin of a human body, it is not possible to place the sample inside the apparatus. In that case, the apparatus should be placed on or against the sample or a part of the sample, whereby the location of the surface to be observed is at the outer side of the apparatus.

An optical measurement device for measuring an optical appearance of a surface of a sample is disclosed in WO 2007/072403. The disclosed device comprises an illumination device for illuminating the surface with an illumination beam and a detection device for detecting the response of the sample to the illumination beam.

In the case that the sample is of a semitransparent material, the light from the light source not only reflects on the surface of the sample, but also penetrates in the sample. The penetrated light scatters inside the sample and will at least be partially absorbed inside the sample, which is characterized by a so-called extinction length, which is a measure for the distance over which all of the penetrated light will be absorbed. Hence, only a part of the penetrated light will be absorbed in the case that the size of the illuminated region is relatively small compared to the extinction length of the penetrated light. If not all of the penetrated light is absorbed, a part of the penetrated and scattered light will emit from the surface of the sample. The observance of the reflected light is then disturbed by the scattered light that emits from the surface of the sample. Therefore, the accuracy of the observation of the appearance of the sample will be relatively poor in the case that the size of the illuminated region is relatively small compared to the extinction length of the penetrated light.

SUMMARY OF THE INVENTION

It is an object of the invention to provide an apparatus for observing the appearance of the surface of a sample of a semitransparent material, wherein the influence of emitted scattered light on the accuracy of the observation of the appearance of the sample is minimized. The invention is defined by the independent claims. Advantageous embodiments are defined by the dependent claims.

This object is achieved by the apparatus for observing the appearance of the surface of a sample of a semitransparent material according to the invention which comprises a light source for illuminating at least a region of interest of the surface of the sample from a predetermined direction and means for observing a response to the illumination of the region of interest, wherein the illuminated region comprises the region of interest and a region surrounding the region of interest. In this way the amount of light that is scattered in the semitransparent material and emitted in the region of interest is relatively small compared to the light reflected directly from the surface and a sub-surface in the region of interest of the sample, because the illuminated region is larger than the observed region of interest. Furthermore, by confining the region of interest with respect to the illuminated region, a light emitting region surrounding the illuminated region and the edge region of the illuminated region, in which regions the amount of emitted light is largely influenced by the scattered light that disturbs the characterization of the surface of the sample, are excluded from the observance of the appearance of the surface of the sample. In fact, the size of the region surrounding the illuminated region, from which light is emanating, is a measure for the extinction length of the light scattered in the semitransparent material.

In a preferred embodiment of the apparatus according to the invention, the surface of the sample is deformable and a translucent plate is placed on the deformable surface having an opening that coincides with the region of interest. When a plate is placed on a deformable surface of a sample, the deformable surface will tend to bulge because of the pressure applied on the surface of the sample. This causes a deformation of the surface which reduces the accuracy of the observation of the sample, for example because the region of interest is deformed and has another focus point. Furthermore, in the case of human skin the texture, color and/or appearance of the surface of the human skin alters under the influence of the mechanical contact of the plate on the human skin. The translucent plate according to the invention reduces the area over which the deformable surface can deform and hence, also the amount of deformation. In a further embodiment the translucent plate comprises illuminant and color standards and a dimension scale, which allows color point correction and calibration In an embodiment of the apparatus according to the invention, the size of the illuminated region is at least two times the extinction length of light penetrated in the sample larger than the size of the region of interest. This optimally minimizes the disturbance of the scattered light on the observed reflected light.

In an embodiment of the apparatus according to the invention, the location of the light source is adjustable, so that the surface of the sample can be illuminated from different predetermined directions, i.e. the incident light beam hits the surface of the sample at different angles. Thereby, a camera can record representations whereby the surface is illuminated differently, so that more information of the surface can be obtained.

In an embodiment of the apparatus according to the invention, the apparatus further comprises an optical focus device for determining if the observing means is in focus with at least a part of the surface of the region of interest. This advantageously provides for safeguarding that the surface of the region of interest is in focus with the means for observing the region of interest, such as for example a camera, and thereby improves the quality of the observation of the appearance of the sample.

BRIEF DESCRIPTION OF THE DRAWINGS

These and other aspects of the invention will be further elucidated and described with reference to the drawings, in which.

The Figures are not drawn to scale. The figures are only schematic and diagrammatic representations, showing only parts of the apparatus that are relevant for the elucidation of the invention. In general, identical components are denoted by the same reference numerals in the Figures.

DETAILED DESCRIPTION OF EMBODIMENTS

Figure 1:
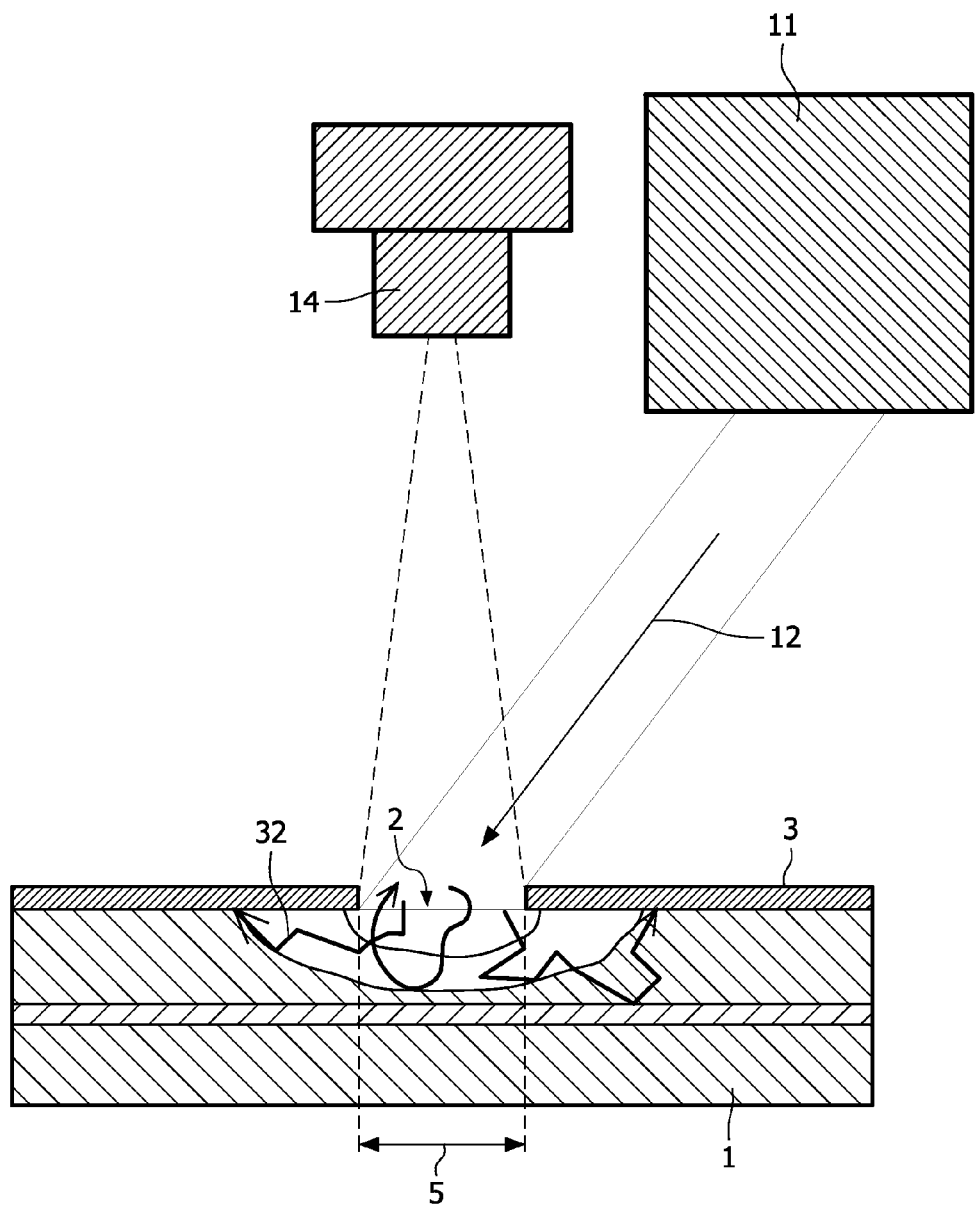
FIG. 1 shows a cross-sectional schematic view of an apparatus for observing the appearance of the surface of a sample as is known in the art.

FIG. 1 shows the principle of an apparatus as is known in the art in a schematic cross-sectional view. It represents diagrammatically a semitransparent or translucent sample 1 having a surface 2 to be observed in order to record and analyze that surface 2. The sample 1 is located underneath the base plate 3 of the apparatus for observing the surface 2. The base plate 3 has a central opening 5. The surface 2 is located in the opening 5. The surface 2 is illuminated by means of a light source 11. Light source 11 directs its light beam 12 to the opening 5. Furthermore, a detector for the observance of the light reflected from the surface 2 in response to the illumination by the light source 11, in this example a camera 14, is present to observe the appearance of the surface 2 onto which the light beam 12 is directed. Instead of or in addition to the camera 14, a color detector or a spectrometer can be applied for observing the response of the surface 2 to the illumination by the light source 11. As is shown in FIG. 1, the opening 5 defines both the part of the surface 2 that is illuminated by the light beam 12 and the part of the surface 2 of which the appearance is observed, also called the region of interest of the sample 1. Part of the light beam 12 will reflect from the surface 2 and will be detected by the camera 14, and part of the light beam 12 penetrate the translucent sample 1 through the surface 2 and will scatter inside the sample 1 as is illustrated by the line arrows 32. Part of the penetrated and scattered light 32 will be absorbed in the sample 1, but a part of this scattered light 32 will scatter such that it emits from the surface 2, and will therefore mix with the part of the light that is reflected directly on the surface 2. This emitting from the surface depends, amongst others, on the extinction length of the penetrated light 32. The extinction length is a measure for the length or distance which the penetrated light travels in the sample 1 before it is totally absorbed in the sample 1. If the extinction length is large with respect to the dimension of part of the surface 2 that is illuminated by the light beam 12, then a large part of the scattered light 12 will emit from the surface 2. In this way the penetrated, scattered and emitted light 32 disturbs the observance of the appearance of the surface 2, which results in a less accurate and disturbed detection of the appearance of the surface 2 by the camera 14.

Figure 2:
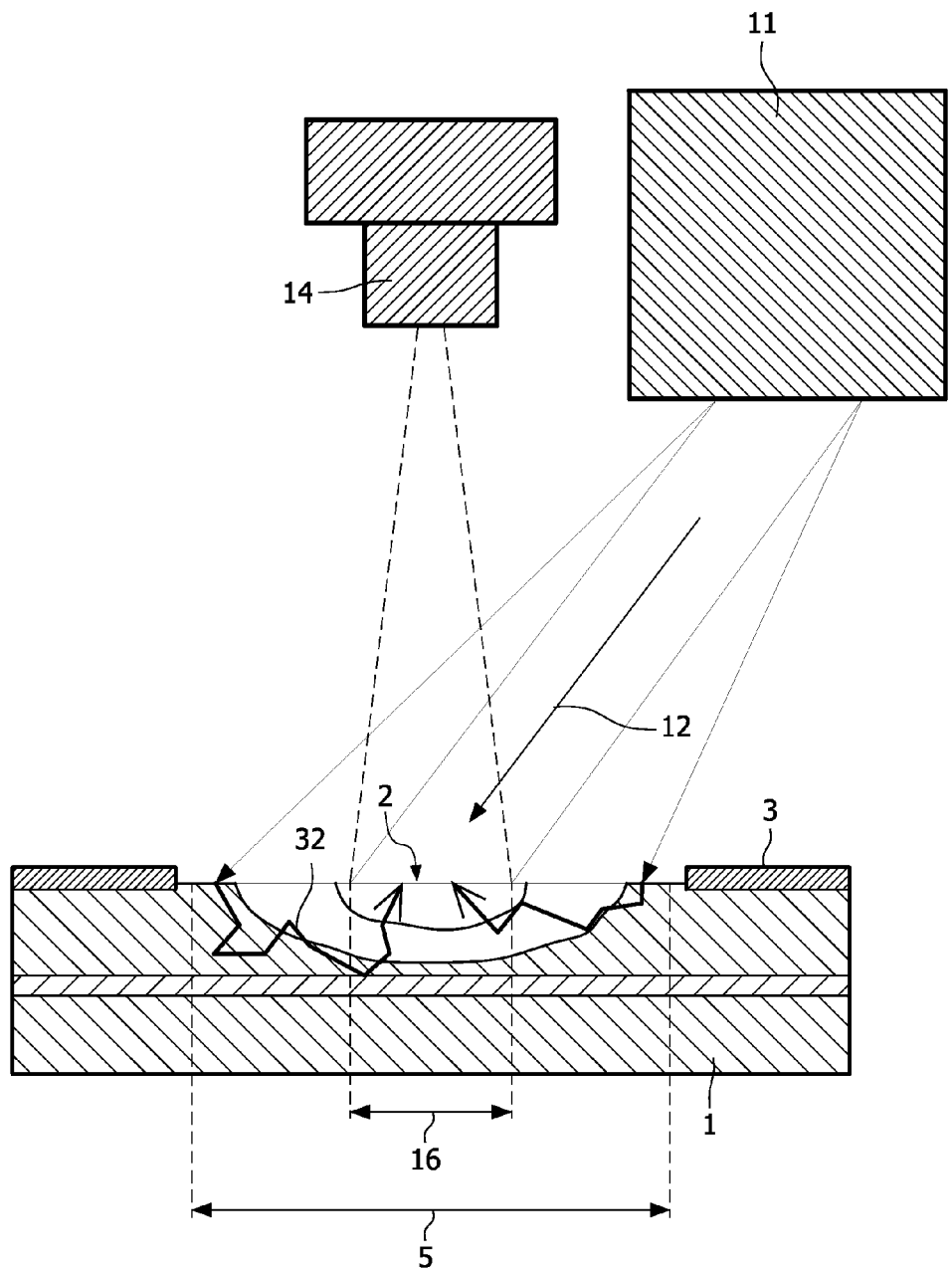
FIG. 2 shows a first embodiment of an apparatus for observing the appearance of the surface of a sample according to the invention.

In FIG. 2 the principle of a first embodiment of an apparatus according to the invention is shown in a schematic cross-sectional view. The central opening 5 is in the apparatus according to the invention larger than the region of interest 16, which is the part of the surface 2 that is observed by the camera 14. The light beam 12 illuminates the part of the surface 2 that is exposed by the opening 5 of the base plate 3. The part of the light beam 12 that reflects from the surface 2 in the region of interest 16 will be observed by the camera 14. The light 32 that penetrates and scatters in the sample 1 will partly be absorbed in the sample 1 and partly emit from the sample 1. However, because in this case only a part of the illuminated region of the surface 2 is observed by the camera 14, also only a relatively small part of the scattered light 32 emits from the region of interest 16. The dimension of the illuminated region, which is defined by the dimensions of the opening 5, is in this case relatively large compared to the extinction length of the penetrated and scattered light 32, which results in that a smaller part of the penetrated light 32 will emit from the region of interest 16, which has a smaller dimension that the opening 5. In this way the observance of the appearance of the surface 2 of the sample 1 is less disturbed by the emitted scattered light 32 resulting in a more accurate picture of the appearance of the surface 2. The dimension of the opening 5 and of the region of interest 16 may be a diameter of a circle or an area of, for example, a circle, rectangle or square.

Figure 3:
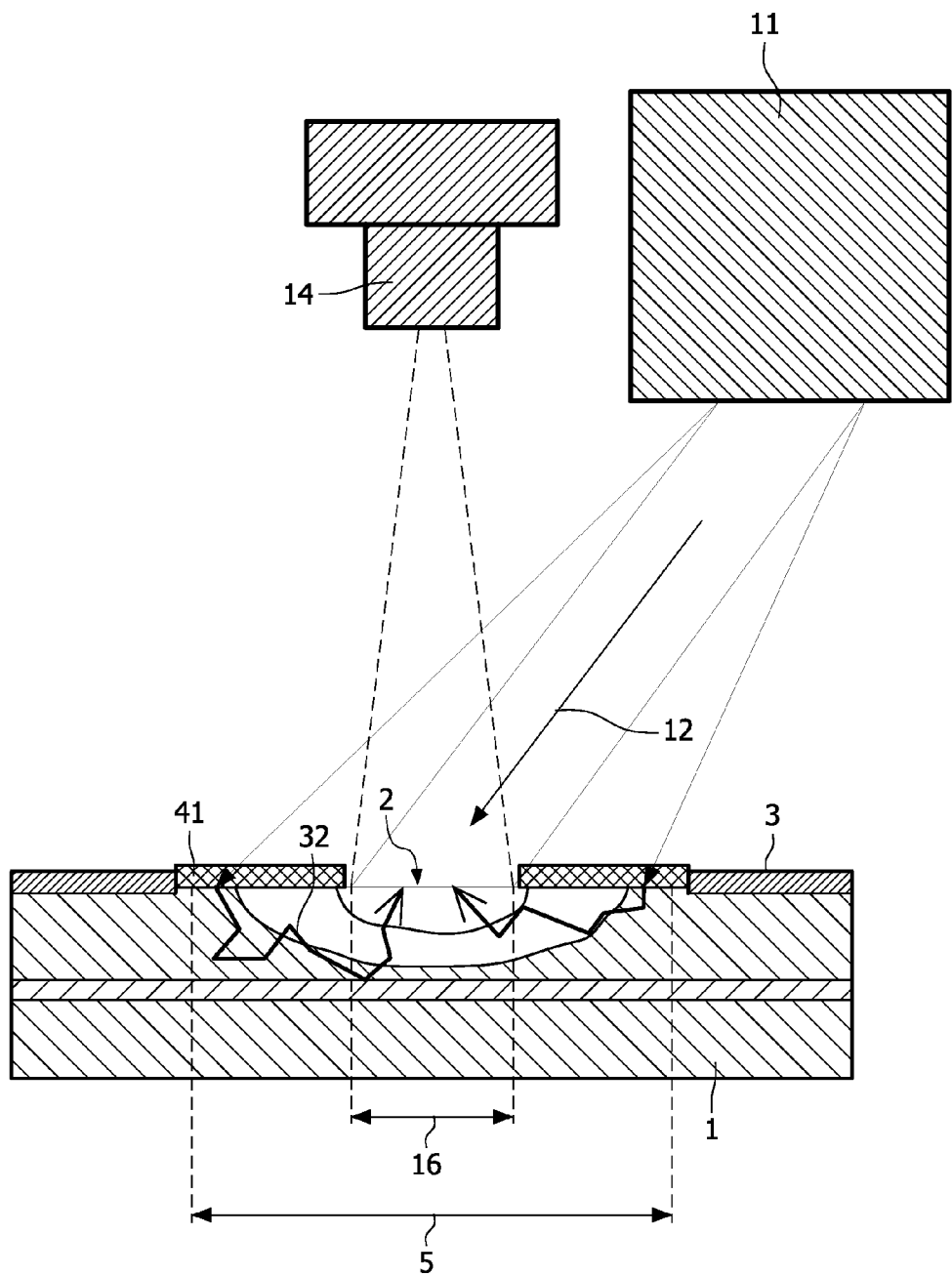
FIG. 3 shows a second embodiment of an apparatus for observing the appearance of the surface of a sample according to the invention.

In FIG. 3 the principle of a second embodiment of an apparatus according to the invention is shown in a schematic cross-sectional view. In this case the translucent sample 1 is deformable and is, for example, skin of a human. The base plate 3 touches the skin and will result in a deformation of the skin that is present in the opening 5 of the base plate 3. Normally, the skin will tend to bulge inwards because of the pressure applied by the base plate 3 on the sample 1. This disturbs the observance of the surface 2 by the camera 14, because the surface 2 will be out of focus and, for example in the case of human skin, the appearance, for example color, is altered. To minimize the deformation of the surface 2 a translucent plate 41 is placed inside the opening 5 wherein the translucent plate 41 has an opening that corresponds to the region of interest 16 which is observed by the camera 14. The light beam 12 illuminates the part of the surface 2 that is exposed by the opening 5, because the plate 41 is translucent. Furthermore, only the part of the surface 2 of the deformable sample 1 that is exposed by the opening of the translucent plate 41 may deform or bulge. The deformation is in this embodiment smaller that the deformation of the surface 2 in the case that no translucent plate 41 is present. Therefore, the disturbance on the observance by the deformation of the surface 2 is minimized. Furthermore, the effect of the first embodiment, in which the observance of the appearance of the surface 2 of the sample 1 is less disturbed by the emitted scattered light 32, is safeguarded by the application of a light transparent material for the plate 41 and the illuminated area that is larger than the region of interest 16. The translucent plate 41 may have a circular or a rectangular opening corresponding to the region of interest 16. A dimension scale can be added on the translucent plate 41, for example near the opening of the translucent plate 41. In addition or next to the dimension scale, illuminant and color standards can be added to the translucent plate 41, which allows color point correction and calibration.

To safeguard that the camera 14 is in focus with at least a part of the surface 2 of the sample 1 that is observed, an optical focus device is added to the apparatus according to the invention. The optical focus device determines if the camera 14 is in focus with at least a part of the surface 2 of the region of interest 16 and, for example, then triggers the observing camera 14 to start the measuring sequence comprising the observation of the appearance of the surface 2.

In summary, the invention relates to an apparatus for observing the appearance of a surface of a sample of semitransparent material, the apparatus comprising a light source for illuminating at least a region of interest of the surface of the sample from a predetermined direction and means for observing the light reflected from the region of interest, wherein the illuminated region comprises the region of interest and a region surrounding the region of interest. In this way the influence of emitted scattered light on the accuracy of the observation of the appearance of the sample is minimized.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of other elements or steps than those listed in a claim. The word "a" or "an" preceding an element does not exclude the presence of a plurality of such elements.

The invention claimed is:

1. An apparatus for observing the appearance of a surface of a sample of semitransparent material, the apparatus comprising:
   a first plate for covering the sample with a first central opening through the first base plate for exposing at least a region of interest of the surface of the sample;
   a translucent second plate sized to fit within the first opening, the second plate comprising a second central opening through the second base plate that coincides with the region of interest;
   a light source for illuminating through the first opening at least the region of interest of the surface of the sample from a predetermined direction; and
   means for observing through the second opening a response to the illumination of the region of interest, wherein the illuminated region comprises the region of interest and a region surrounding the region of interest.

2. The apparatus as claimed in claim 1, wherein the second plate comprises illuminant and color standards and a dimension scale.

3. The apparatus as claimed in claim 1, wherein a size of the illuminated region through the first opening is at least two times an extinction length of light from the light source penetrated in the sample thereby, minimizing a contribution of scattered light to the response.

4. The apparatus as claimed in claim 1, wherein a location of the light source is adjustable, so that the surface of the sample can be illuminated from a plurality of predetermined directions.

5. The apparatus as claimed in claim 1, further comprising an optical focus device configured to
   determine if the observing means is in focus with at least a part of the surface of the region of interest; and
   trigger the observing means to observe the response when it is determined that the observing means is in focus.

* * * * *